United States Patent [19]

Stuchlík et al.

[11] Patent Number: 5,670,478

[45] Date of Patent: Sep. 23, 1997

[54] PHARMACEUTICAL CONTAINING N-METHYLATED CYCLIC UNDECAPEPTIDES

[75] Inventors: Milan Stuchlík; Zdeněk Pavelek; Luboš Markovič, all of Opava, Czech Rep.

[73] Assignee: Galena, a.s., Czech Rep.

[21] Appl. No.: 387,914

[22] PCT Filed: Sep. 3, 1993

[86] PCT No.: PCT/CZ93/00022

§ 371 Date: Feb. 22, 1995

§ 102(e) Date: Feb. 22, 1995

[87] PCT Pub. No.: WO94/05312

PCT Pub. Date: Mar. 17, 1994

[30] Foreign Application Priority Data

Sep. 7, 1992 [CS] Czechoslovakia .......... 2770-92

[51] Int. Cl.⁶ .......... A61K 38/00; A61K 38/12; C07K 5/00; C07K 7/00

[52] U.S. Cl. .......... 514/11; 514/9; 514/885; 530/317

[58] Field of Search .......... 530/317; 514/9, 514/11, 885

[56] References Cited

U.S. PATENT DOCUMENTS

| | | | |
|---|---|---|---|
| 3,951,945 | 4/1976 | Heesen et al. | 260/210 |
| 4,388,307 | 6/1983 | Cavanak | 424/177 |
| 4,996,193 | 2/1991 | Hewitt et al. | 514/11 |

FOREIGN PATENT DOCUMENTS

| | | | |
|---|---|---|---|
| 277 472 | 2/1993 | Czechoslovakia | C07K 7/54 |
| 0 242 205 | 10/1987 | European Pat. Off. | A61K 39/00 |
| 0 296 122 | 12/1988 | European Pat. Off. | A61K 37/02 |
| 0 321 128 | 6/1989 | European Pat. Off. | A61K 37/02 |
| A 2 608 427 | 6/1988 | France | A61K 9/14 |
| 589 716 | 7/1977 | Switzerland | C12D 9/04 |
| 603 790 | 8/1978 | Switzerland | C12D 9/04 |
| 636 013 | 5/1983 | Switzerland | A61K 45/08 |
| WO87/06463 | 11/1987 | WIPO | |
| 9003793 | 4/1990 | WIPO | |
| WO90/03793 | 4/1990 | WIPO | A61K 37/02 |

OTHER PUBLICATIONS

Descotes et al., Immunotoxicity Screening of Drugs & Chemicals: Value of Contact Hypersensitivity of Picryl Chloride in the Mouse, 1985, pp. 303–305.

Matha et al., The Mosquitocidal Activity of Conidia of *Tolypocladium tundrense* and *Tolypocladium terricola*, 1992, pp. 163–170, Great Britain.

Traber et al., Isolation & Structure Determination of the New Cyclosporins E, F, G, H and I, 1982, pp. 1655–1677.

Lorenz et al., Histamine release & hypotensive reactions in dogs by solubilizing agents & fatty acids: Analysis of various components in cremophor El and development of a compound with reduced toxicity, 1982, vol. 12, pp. 64–80.

Wood et al., Cyclosporine: Pharmacokinetics, Metabolism and Drug Interactions. Transplantation Proc. XV, 4, Suppl. 1, 2409–2412, 1983, Switzerland.

*Primary Examiner*—Cecilia J. Tsang
*Assistant Examiner*—Michael Borin
*Attorney, Agent, or Firm*—Zarley, McKee, Thomte, Voorhees, & Sease

[57] ABSTRACT

Medical preparations (drugs) containing N-methylated cyclic undecapeptides, especially for internal use, characterized by the presence of 0.1 to 20 weight parts of compounds from the group of cyclosporins (A), 0.3 to 60 weight parts of emulsifier (B) containing anhydromanitol oleylether and/or lactoglyceride and/or citrogylceride, 0.1 to 10 weight parts of emulsion stabilizer (C) containing aluminium-magnesium hydroxy-stearate as a lipogel and 0.2 to 40 weight parts of a solvent (D) composed of 1,4: 3,6-dianhydro-2,5-di-O-methyl-D-glucitole and/or 1,3-dimethyl-2-imidazolidone and/or ethanol, with the ratio A:B being equal to 1:05–1:30.

6 Claims, 3 Drawing Sheets

PHARMACEUTICAL CONTAINING N-METHYLATED CYCLIC UNDECAPEPTIDES

TECHNICAL FIELD

The present invention concerns medical preparations for internal use, or for another use, containing poly-N-methylated monocyclic undecapeptides called cyclosporins.

BACKGROUND ART

This group of stucturally similar peptides called cyclosporins is produced by some deuteromycetes, such as e.g. Tolypocladium inflatum (Swiss pat. 589 716 and 603 790) or Tolypocladium terricola (Matha et al., Cytobios 69, 163–170, 1992). Besides cyclosporin A (=cyclosporin) of formula I a number of structurally similar natural cyclosporins was isolated (Traber et al., Helv. Chim. Acta 65, 1655–1667, 1982). Modified cyclosporins which were prepared by partial synthesis were described also in EPA 0216 122 or in Czechoslovak patent 277 472.

Especially immunosuppressive properties of systemically administered cyclosporin are used in therapy or during organ transplants or bone marrow transplants. It is also applicable in treatment of broad range of autoimmune diseases of inflammatory etiology and also as antiparasitic treatment. Cyclosporin is used e.g. in rheumatic diseases (rheumatoid polyarthritis), hematologic diseases (aplastic anemia, idiopathic thrombocytopenia), gastric disorders (ulcerating colitis, Crohn disease), dermatic diseases (psoriasis, sclerodermia) and eye diseases (uveitis). Also topical applications have been tested e.g. in treatment of psoriasis, uveitis and allopecia.

Bioavailability of cyclosporin varies between 20–50% for currently available dosage formulations (Wood A. J., et al., Transplant Proc., 15, suppl. 2409, 1983). There are significant differences between groups of patients. E.g. there is a low bioavailability in liver acceptors, and increased bioavailability in bone marrow transplantation. The interpersonal variability of biovailability is considerably greater, ranging from a few percent to 90%. This is complicated also by the presence of significant variations in the course of the treatment.

Effective immunosuppressive treatment requires keeping a certain level of cyclosporin in blood and maintaining this level in certain range. The range required is always specific depending upon therapeutic goal. E.g. in cases of graft rejection or in treatment of autoimmune disease, it is necessary to take into account application of another immunosuppressant at the same time. When formulating medical drugs with cyclosporins, it is important to take into account their high lipophilicity. Solubility of these drugs in water varies usually from 1.6–2.3 mg/100 ml and does not exceed 4 mg/100 ml. Cyclosporins are not sufficiently resorbed from usual carriers in both liquid or solid state. This problem is solved in Swiss patent 636013 by using sezame oil and/or non-ionogenic tenside and/or reesterified non-ionogenic triglyceride and/or a mixture containing one or more lecithins, reeesterified non-ionogenic triglycerides or ethyloleate and/or neutral oil.

I

Another Swiss patent 641356 is trying to improve resorption of cyclosporins by adding transesterification products of triglycerides with polyethylenglycols and/or saturated triglyceride of fatty acid and/or mono or diglycerides.

Therapeutically suitable concentrations of cyclosporins in liquid carriers show low stability towards precipitations from the solutions and the solutions are usually badly tolerated. Injection preparations containing a non-ionogenic tenside (Cremophor EL) can develop the anaphylactic reaction (Lorenc W. et al.: Agents and Actions 12, 64–80, 1982) and cause washing out of additives from plastic parts of devices for parenteral applications.

An oral formualtion with transesterification product of triglyceride with polyethylenglycols (Labrafil® M1944 CS) forms an emulsion of v/o type in which phases are easily separated.

Insufficient tolerance of injection cyclosporin preparations containing non-ionogenic tensides was solved in a French patent 2608427 by preparing a lyophilisate for ad hoc formulation of sub-microne suspension. However, this process is energy-consuming when working with larger volumes of carrier containing ethanol.

Frequent undesirable side effects of cyclosporin treatment include nephrotoxicity, hypertension, hyperkalemia, hyperurikemia, hepatotoxicity, anemia, gastrointestinal intolerance, tremor and parestesia. The most frequent side effect is usually renal dysfunction. Acute cyclosporin nefrotoxicity is dose-dependent. There is a correlation with the blood level and a decrease in the dose or discontinuation of cyclosporin therapy leads to an improvement. However, progressive and irreversible damage of kidneys was reported in patients with transplants.

A composition of cyclosporin preparation with decreased nephrotoxicity containing omega 3 group of unsaturated fatty acids from fish oils was described in published international patent application WO 87/06463. A disadvantage of this form is considerable instability of the polyunsaturated fatty acids towards oxidative effects and unpleasant taste and odour.

The same is possible to say about similar cyclosporin formulations based on esential unsaturated fatty acids of evening primrose oil (Oenothera biennis and Oenothera Lamarckiana), borago oil (Borago officinalis) covered by published international patent application WO 90/03793 or black currant oil (Ribes nigrum) which is described in published european patent application EP 0 321 128.

DISCLOSURE OF INVENTION

The principle of new pharmaceutical preparations with N-methylated cyclic undecapeptides, which are developed especially for internal use, is in the fact that they contain 0.1 to 20 weight parts of compounds /A/ from the group of cyclosporins, 0.3 to 60 weight parts of an emulsifier /B/ composed of anhydromannitol oleylether and/or lactoglyceride and/or citroglyceride, 0.1 to 10 weight parts of emulsion stabilizer /C/ composed of aluminium-magnesium hydroxystearate of empirical formula $Al_5Mg(OH)_{31} \cdot (C_{17}H_{35}COO)_4$ in a form of lipogel and 0.2 to 40 weight parts of a solvent /D/ composed of 1,4:3,6-dianhydro-2,5-di-O-methyl-D-glucitole and/or 1,3-dimethyl-2-imidazolidinone and/or ethanol. The ratio A:B is from 1:0,5 to 1:30.

The compounds from the group of cyclosporins are either cyclosporin or /NVa/$^2$ cyclosporin. The medical drugs prepared according to the present invention may contain also physiologically acceptable carrier based upon synthetic or plant oil with interfacial tension 10 $mN.m^{-1}$ to 25 $mN.m^{-1}$. Lactoglyceride or citroglyceride contain preferably at least 90% of compound of general formula where at least one of the $R_1$, $R_2$, or $R_3$ substituents represents a lactic or citric acid moiety, one represents a fatty acid moiety $C_{14}$ to $C_{18}$ and the remainder is selected from the group consisting of lactic acid moiety, citric acid moiety, fatty acid moiety $C_{14}$ to $C_{18}$ and hydrogen. The medical preparations for external application contain preferably 1,3-dimethyl-2-imidazolidinone as a solvent.

The preparations according to the invention are proposed as self-emulgating dispersions of water/oil type stabilized by lipogel of aluminium-magnesium hydroxystearate. The emulsion part consists of a mixture of non-ionogenic tensides with the individual value HLB equal to 4–11, which do not contain ethyleneoxide units. With regard to characteristic emulgation properties of the tensides used, the external continuous lipophilic phase is selected in such a way as to be formed of more polar oils with polarity index 10–25 $mN.m^{-1}$. Amphiphillic liquids of higher boiling point are used as solvents of cyclosporins. These liquids are miscible with water and most of organic solvents. They consist of 1,4:3,6-dianhydro-2,5-di-O-methyl-D-glucitole and 1,3-dimethyl-2-imidazolidinone or physiologically acceptable ethanol. The emulsifier anhydromanitol oleylether/ Montanide® 103 is a liquid of HLB 6.5 which is biodegradable by pancreatic lipases after oral application. It is characterized by the following physico-chemical parameters:

| | |
|---|---|
| density/20° C./ | 0.97 |
| viscosity/25° C./ | cca 350 mPa · s |
| index of refraction /23° C./ | 1.474–1.475 |
| iodine number | 51–60 |
| saponification number | 120–136 |
| hydroxyl number | 95–110 |
| acidity number | max. 1.5 |
| peroxide number | max. 2.0 (mmol/kg) |

Citroglycerides and lactoglycerides form the second group of emulsifiers used in the preparations made according to the invention. These are composed of mixed triacylglycerols where one or two hydroxyl groups are esterified by fatty acids and two or one glycerole hydroxyl is esterified by lactic acid or citric acid. These emulsifiers are made in several commercial brands, especially for food industry and they are marketed under the trade mark AXOL (Th. Goldschmidt AG). Lactoglyceride AXOL L61, L62 and citroglyceride AXOL C62 are typical representatives of these emulsifiers and they are characterized by the following physico chemical parameters:

| | AXOL L61 | AXOL L62 | AXOLC62 |
|---|---|---|---|
| melting point | 48–53° C. | ≈45° C. | 58–64° C. |
| saponification number | 220–260 | >295 | 215–265 |
| iodine nummr | max. 3 | max. 3 | max. 3 |
| free fatty acids | max. 3% | max. 3% | max. 3% |
| HLB | 5 ± 1 | 6 ± 1 | 10 ± 1 |

Metabolic studies showed that these emulsifiers were totally hydrolyzed in the gastrointestinal tract giving rise to glycerol, fatty acids and corresponding hydroxycarboxylic acids. Experiments with labelled hydroxycarboxylic acids showed that metabolism of acids bonded by an ester group was not significantly different from that of free hydroxycarboxylic acids.

It is generally known that formation of stable emulsion of v/o type is more demanding as far as mechanical and thermal energy is concerned. Special devices or elevated temperature may be required in emulgating processes in situ in which the dispersion is formed when needed, e.g. before dilution, before application or during contact with body fluids. It is however desirable to achieve homogenous dispersion without special devices or elevated temperature. This can be achieved by special additives adjusting rheology. These additives can be in a form of lipogel aluminium magnesium hydroxystearate in plant oils. These lipogels are commercially available as GILUGEL (Giulini Chemie). For the preparations according to the present invention, the following types are most suitable: Gilugel MIG containing 80% of neutral oil MIGLYOL 812, Gilugel ALM containing 80% of almond oil and Gilugel CAO containing 80% of castor oil. Gilugel MIG and Gilugel ALM are characterized by the following physico chemical data:

|  | Gilugel MIG | Gilugel ALM |
|---|---|---|
| content of Al | 0.7–1.4% | 0.7–1.4% |
| content of Mg | 1.7–2.8% | 1.7–2,8% |
| content of $Al_5Mg_{10}/OH/_{31}/C_{17}H_{35}COO/_4$ | 20% | 20% |
| content of water | 0.4–1.2% | 0.1–0.4% |
| density | 0.985–0.995 | 0.97 |

Figure 1:
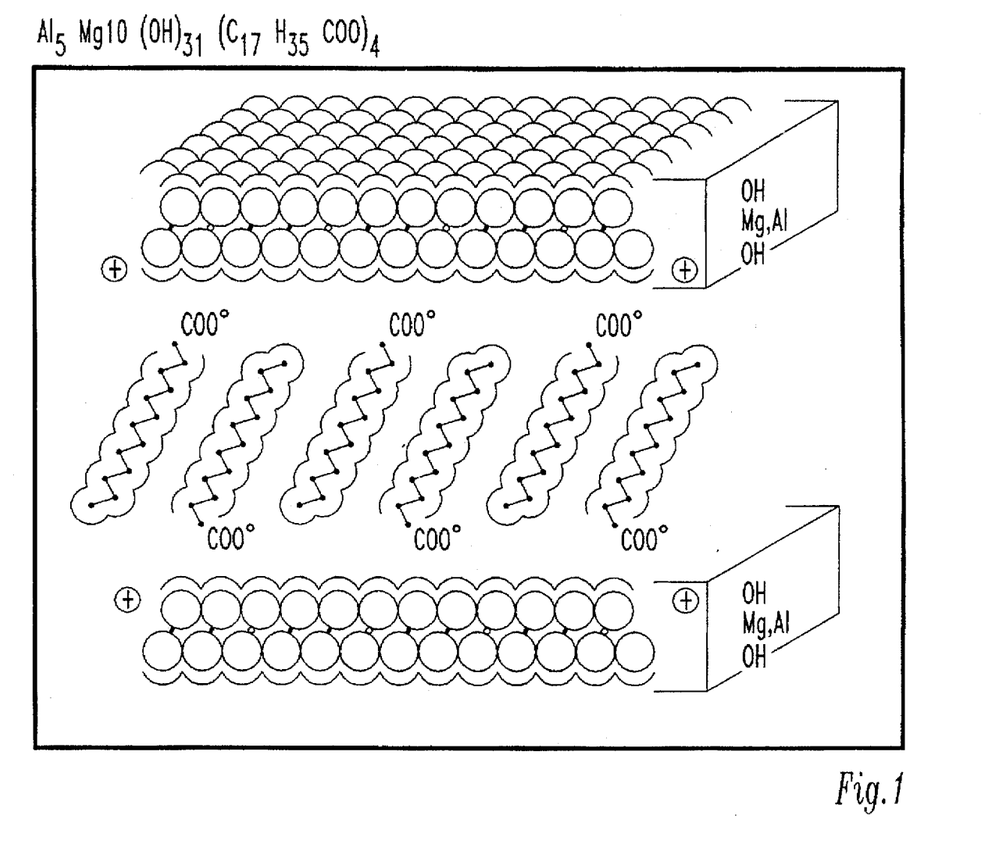
FIG. 1 depicts a scheme of multi-layered grid structure of aluminium-magnesium hydroxystearate of empirical formula $Al_5Mg_{10}(OH)_{31} \cdot (C_{17}H_{35}COO)_4$.

The multilayer grid structure of Gilugel is characterised in scheme FIG. 1.

Figure 2:
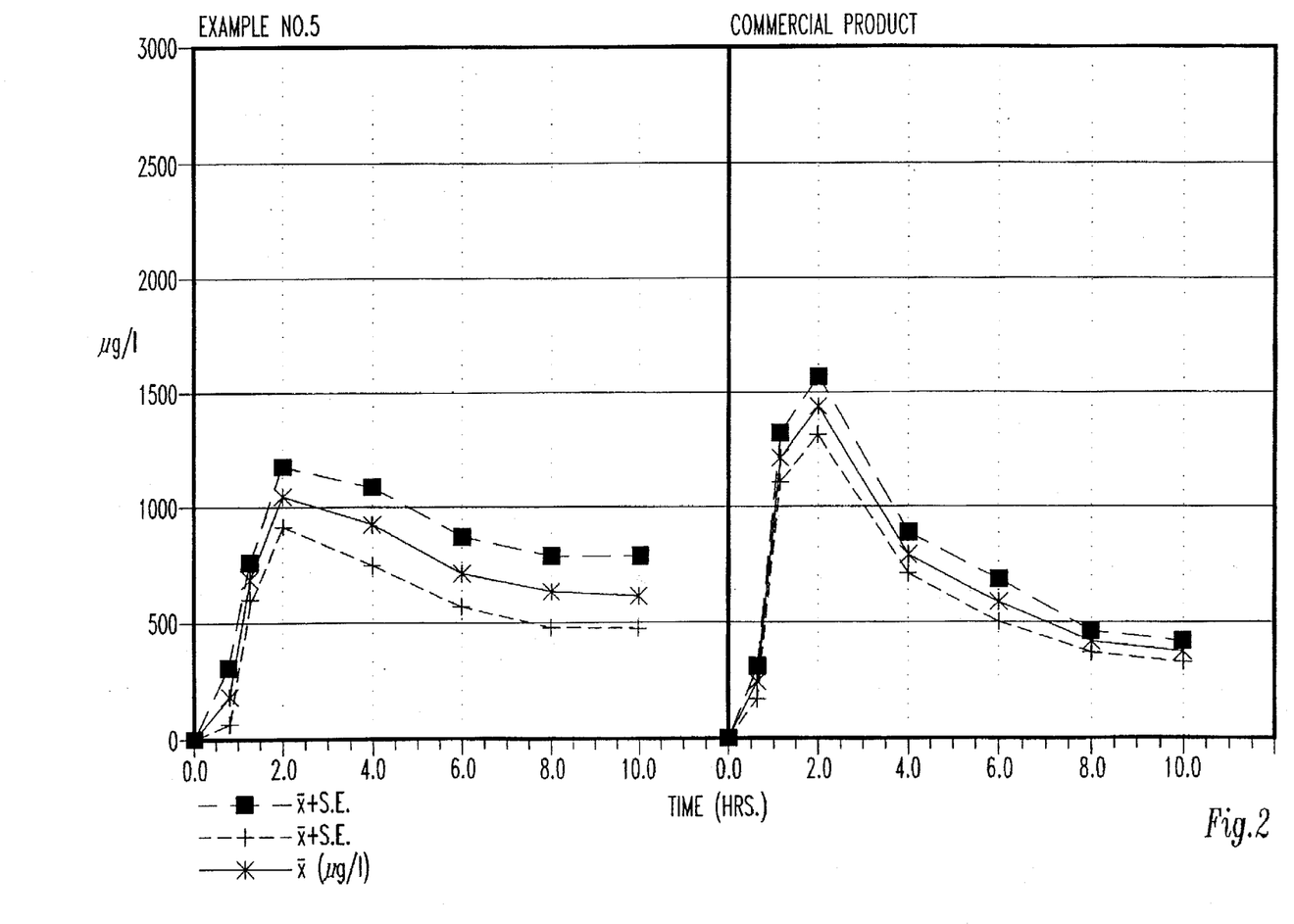
FIGS. 2 and 3 shows graphs comparing a dependence of cyclosporin concentration in blood on time after application of the preparation according to invention and commercial product to Beagle dogs. The determination of the blood levels was made by means of RIA methods with specific antibodies (FIG. 2) and non-specific antibodies (FIG. 3).
Figure 3:
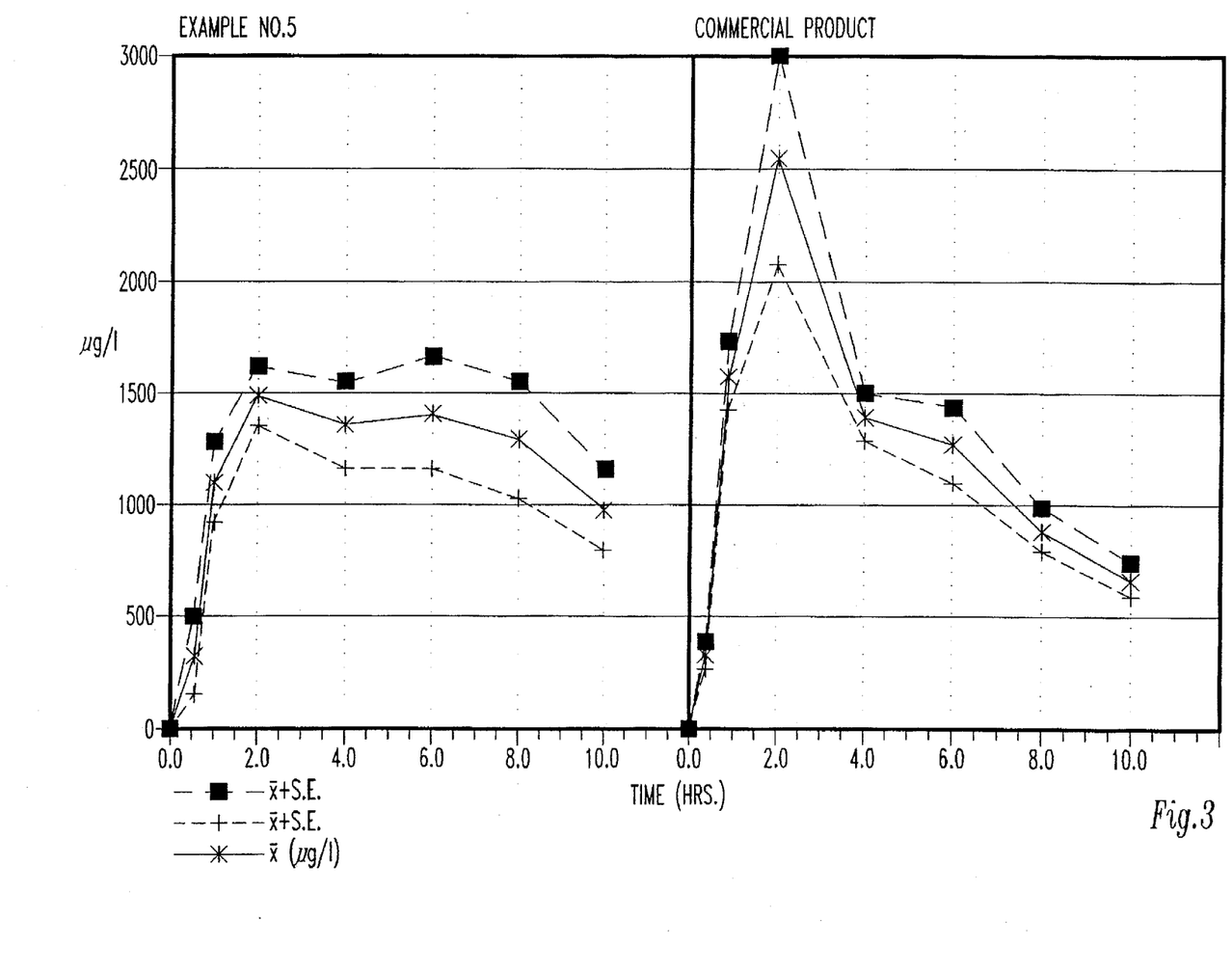

Modified—release of cyclosporin is achieved by arrangement of the ratio of emulsifiers and stabilizing agent. It is documented by FIG. 2 and FIG. 3 where time dependencies of blood levels are compared for commercially available product and for the preparation according to the present invention when applied to Beagle dogs.

In relation to emulsifiers used, triacylglycerols are suitable carriers, provided their polarity, expressed as the interfacial tension, is in the range 10–25 $mN.m^{-1}$. For example the following oil can be used: castor oil/13.7/, milk thistle oil/14.8/, olive oil/16.9/, almond oil/20.3/, and Miglyol 812 /21.3/.

Favourable for use in the preparations according to the invention is the milk thistle oil, prepared from the seed of Silybum marianum by cold pressure or solvent extraction. The fatty acids part of the oil comprises:

| palmitic acid | 7.5–12.5% |
|---|---|
| stearic acid | 3.5–6.5% |
| oleic acid | 20.0–35.0% |
| linoleic acid | 46.0–65.0% |
| linolenic acid | up to 5.0% |
| gadolenic acid | up to 1.0% |
| behenic acid | up to 2.5% |

The solvent 1,4:3,6-dianhydro-2,5-di-O-methyl-D-glucitol under the name Arlasolve DMI is produced by the company ICI American Inc. It has the following physico chemical properties:

| boiling point | approx. 234° C. |
|---|---|
| density 25° C. | 1,164 |
| refractive index | 1,467 |
| viscosity 25° C. | approx. 5 mPa · s |
| dielectric constant | approx. 7 |

The solvent 1,3-dimethyl-2-imidazolidinone is produced by Mitsui Toatsu Chemicals. Both compounds are characterized by high dissolving power for cyclosporins. 1,3-dimethyl-2-imidazolidinone is especially suitable for topical formulations due to its structural similarity with urea which improves skin hydration.

Preparations according to present invention were verified in two pharmacological models in 3 concentrations as described further on.

Influence of topical cyclosporin upon contact dermatitis induced in guinea pigs by 2,4-dinitrofluorobenzene (DNFB).

The topical preparation was tested in three concentrations (2%, 1% and 0.1%) against placebo.

Albine twings (females, weight 300–500 g) were used. The animals were sensitized on the base of both ears by 50 μl of 2% or 5% DNFB (Aldrich Chemie, Germany) dissolved in a mixture of acetone—olive oil (1:1). The animals were shaved and depilated after 6 days (Opilca) on both sides. On the following day, 20 μl of 0.5% DNFB dissolved in a mixture aceton: olive oil (4:1) was applied on both sides. Immediately afterwards, 250 mg of the cyclosporin was applied on the right side while 250 mg of the placebo was applied on the lift side. Two controls were used in the experiment—control 1 (negative with only 20 μl of 0.5% DNFB being applied to both sides) and control 2 (positive, non treated with the compounds tested). The following parameters were assessed: skin thickness (measured one day before, 8, 24, 32, 48 hours after application) and erythrema (evaluated 24 and 32 hours after application). A size of the oedema was determined by subtracting the values measured one day before the application. The erythrema was assessed according to the following scale: 4—protruding and dark red spot, 3—red spot, 2—pink spot, 1—spread small points of pink colour, 0—no change. The experiment was repeated twice —the animals were sensitized by 5% or 2% DNFB.

The effect of the compounds tested upon the oedema is depicted in the FIGS. 1a and 1b. Cyclosporin influenced positively development of the oedema in comparison with the placebo with all concentrations used. The effect of the compounds upon the erythrema is summarized in the following table. Statistical evaluation was performed by Student t-test. Abbreviation CY A is used for cyclosporin (cyclosporin A).

Sensibilization with 5% DNFB

|  | no. of | erythrema | |
|---|---|---|---|
|  | animals | 24 hrs | 32 hrs |
| Control 1 | 3 | 0 ± 0 | 0 ± 0 |
| Control 2 | 5 | 2.40 ± 0.52 | 2.10 ± 0.88 |
| CY A 0.1% | 5 | 0.40 ± 0.55* | 0.60 ± 0.55 |
| CY A 1% | 5 | 0 ± 0*** | 0.20 ± 0.45** |
| CY A 2% | 5 | 0.20 ± 0.45** | 0.20 ± 0.45** |
| placebo | 5 | 1.27 ± 1.03 | 1.13 ± 0.64 |

Sensibilization with 2% DNFB

|  | no. of | erythrema | |
|---|---|---|---|
|  | animals | 24 hrs | 32 hrs |
| Control 1 | 3 | 0.50 ± 0.55 | 0.50 ± 0.55 |
| Control 2 | 5 | 2.20 ± 0.63 | 1.50 ± 0.71 |
| CY A 0.1% | 5 | 0.20 ± 0.45*** | 0.40 ± 0.55* |
| CY A 1% | 5 | 0 ± 0*** | 0.20 ± 0.45** |
| CY A 2% | 5 | 0 ± 0*** | 0 ± 0*** |
| placebo | 5 | 1.67 ± 0.82 | 1.27 ± 1.03 |

Statistical evaluation was performed by Student t-test and was related to placebo.
*$p < 0.05$ $p < 0.01$ *$p < 0.001$ Effect of topical cyclosporin on DTH (a reaction of delayed hypersensitivity) induced by picrylchloride in mice.

The topical preparation was tested in three concentrations 2%, 1% and 0.1% in comparison with cyclosporin placebo.

A modified method was used as described by Descotes et al.: Meth. and Find. Exptl. Clin. Pharmacol., 7(6):303–305, 1985. The inbred mice C57BL10/ScSn (females, weight 18–22 g) were used for the experiment. Abdomens of the animals were shaved on the day 0 and 200 µl of 5% picrylchloride was applied to abdomen and paws. The picrylchloride was dissolved in 100% ethanol. After 7 days, thickness of ears was measured and 50 µl of 1% picrylchloride was applied on both ears. Immediately afterwards, 10 mg of topical cyclosporin was applied to right ear and 10 mg of corresponding placebo was applied to left ear. Ear thickness was measured again after 14 hours. The value of oedema was obtained by subtracting ear thickness after and before the application of picrylchloride. Two controls were used for the experiment: control 1 (negative, only 50 µl of 1% PiCl was applied on both ears) and control 2 (positive, not treated by the compounds tested). Statistical evaluation was performed by Student t-test and related to placebo. Each group contained 10 animals. The following table shows that both cyclosporin and placebo have beneficial effect upon the oedema induced by picrylchloride. A dose dependence was observed for the effect of cyclosporin. 2% concentration was the most effective and showed statistically significantly better than placebo alone.

|  | Oedema (mm) | % |
|---|---|---|
| Control 1 | 0.031 ± 0.015 | 42.5 |
| Control 2 | 0.073 ± 0.030 | 100.0 |
| CYA 0.1% | 0.016 ± 0.016 | 21.9 |
| CYA 1% | 0.015 ± 0.012 | 20.5 |
| CYA 2% | 0.009 ± 0.009*** | 12.3 |
| placebo | 0.024 ± 0.020 | 32.9 |

Application of high-boiling solvents (Arlasolve DMI, b.p. 234° C. or 1,3-dimethyl-2-imidazolidinone, b.p. 225° C.) eliminates familiar problems with storage of existing oral concentrates and gelatine capsules based on ethanol which require a special packaging material. The capsules are usually packed in a single bed alu-foil packaging which makes the preparation rather voluminous and expansive while liquid concentrates require special leak-proof bottles with a rubber stop per secured by an aluminium capsule.

The pharmacokinetic study of preparations according to the invention in comparison to the commercial product was carried out after single oral dose 200 mg of cyclosporin using cross-over method in two phases in nine Beagle dogs. Male animals, aged 12 through 36 month, body weight of 9 to 13 kg. They were feed with standard pelleted diet in daily dose of 300 g witch free access to drinking water. Doses were administered in the morning, after 18 hours starvation and swallowing was checked. Next feed was administered 12 hours later.

Samples of blood were taken in the following intervals: 0–0.5–1–2–4–6–8–10–12–24 hours after administration. Samples were frozen and stored at −20° C. until the amalysis by means RIA method with the specific antibodies, the nonspecific antibodies or HPLC method was done.

In the course of the average concentrations of cyclosporin in blood in the dependence on time, determinated by specific RIA (FIG. 2) and non-specific RIA methods (FIG. 3) in the commercial product and the preparation according to this invention (example 5), there is the evidence to achieve the modified release of cyclosporin in the coarse of first 10 hours after the administration of the preparation according to this invention by decreasing of amount of emulsifier with simultaneous increasing of stabilizing agent in the preparation according to the invention it is possible to increase bioavailability of cyclosporin from separate formulations mentioned in the examples 6 and 2 by the increasing of the portion of emulgator.

| Example No. 6 | | | | |
|---|---|---|---|---|
|  | HPLC Capsules | | HPLC Capsules fill | |
| Time | x̄ [µg/l] | S.E. | x̄ [µg/l] | S.E. |
| 0.5 | 168.00 | 40.62 | 340.20 | 142.27 |
| 1.0 | 721.40 | 152.36 | 819.90 | 87.28 |
| 2.0 | 1259.90 | 199.84 | 1177.30 | 85.446 |
| 4.0 | 951.60 | 189.51 | 753.10 | 78.79 |
| 6.0 | 628.20 | 123.70 | 557.20 | 97.90 |
| 8.0 | 541.00 | 115.62 | 431.10 | 74.22 |
| 10.0 | 521.40 | 100.27 | 368.80 | 70.75 |
| 12.0 | 394.80 | 68.09 | 338.70 | 79.49 |
| 24.0 | 114.50 | 32.13 | 169.70 | 43.52 |

| Example No. 2 | | | | |
|---|---|---|---|---|
|  | HPLC Capsules | | Specific.RIA Capsules fill | |
| Time | x̄ [µg/l] | S.E. | x̄ [µg/l] | S.E. |
| 0.5 | 526.30 | 158.15 | 417.83 | 178.60 |
| 1.0 | 1421.30 | 277.32 | 1416.50 | 253.92 |
| 2.0 | 1634.20 | 215.39 | 1713.33 | 192.49 |
| 4.0 | 1016.80 | 124.19 | 1259.67 | 154.09 |
| 6.0 | 761.20 | 126.27 | 999.06 | 209.70 |
| 8.0 | 648.10 | 137.54 | 799.00 | 122.51 |
| 10.0 | 593.60 | 126.39 | 627.33 | 88.74 |
| 12.0. | 466.80 | 93.98 | 562.33 | 70.49 |
| 24.0 | 190.20 | 49.64 | 197.83 | 52.26 |

It is possible to reach bioequivalence between separate dosage forms as confirm pharmacokinetic data of commercial product and preparation according to the invention, example No. 2.

|  | Commercial product | Example No. 2 |
|---|---|---|
| $AUC_{0-10h}$ | 11790.58 | 14336.42 |
| $C_{max}$ | 1985.50 | 1999.50 |
| $t_{max}$ | 2 | 2 |
| $K_a$ | 3.431 | 3.725 |
| $t_{1/2}^{(a)}$ | 0.202 | 0.198 |
| $K_e$ | 0.215 | 0.173 |
| $t_{1/2}^{(e)}$ | 3.276 | 4.043 |
| MRT | 6.243 | 7.389 |
| $V_d$ | 80.380 | 81.968 |
| CL | 17.357 | 14.514 |

List of abbreviations used

| AVC | area under the curve of concentration − time dependence [µg · l⁻¹ · h] |
|---|---|
| $C_{max}$ | mximum concentration obtained [µg · l⁻¹] |
| $T_{max}$ | time to reach the concentration-time dependence curve peak [h] |
| $K_a$ | first order absorption rate constant [h⁻¹] |
| $t_{1/2}^{(a)}$ | absorption half-life time [h] |
| $K_e$ | first order elimination rate constant [h⁻¹] |
| $t_{1/2}^{(b)}$ | elimination half-life time [h] |
| MRT | mean residend time [h] |
| $V_d$ | volume of distribution [l] |
| CL | total body clearence [l · h⁻¹] |

MODES FOR CARRYING OUT THE INVENTION

The following examples show some compositions of preparations made according to the invention without having any limiting meaning.

1. Soft gelatine capsule

| Composition: | cyclosporin | 1.500 kg |
| --- | --- | --- |
| | Arlasolve DMI | 2.250 kg |
| | Montanide 103 | 2.500 kg |
| | Axol C62 | 0.500 kg |
| | Gilugel MIG | 1.000 kg |
| | Miglyol 812 | up to 12.000 litres |

Method of preparation:

Axol C62 and Miglyol 812 are mixed at 65° C. and Gilugel MIG is disperged into a homogenous mixture. A solution of cyclosporin in Arlasolve DMI and Montanide 103 is added and stirred until the temperature drops to ambient. The preparation is filled into gelatine capsules on a suitable equipment (e.g. Pharmagel Mark III) in such a way that capsules No. 10 and 20 contain 75 and 150 mg of cyclosporin respectively.

2. A concentrate for oral application

| Composition: | cyclosporin | 1.000 kg |
| --- | --- | --- |
| | Arlasolve DMI | 1.500 kg |
| | Montanide 103 | 3.000 kg |
| | Axol L61 | 1.000 kg |
| | Gilugel MIG | 1.000 kg |
| | Milk thistle oil | up to 10.000 litres |

Method of preparation:

Axol L61 is mixed with milk thistle oil at 55° C. and Gilugel MIG is disperged in the homogenous mixture. The dispersion is mixed with a solution of cyclosporin in Arlasolve DMI and Montanide 103 and the mixture is stirred until cooling down to ambient temperature. The preparation is filled into glass ampoules under protective atmosphere of inert gas. The ampoules are marked by volumetric signs.

3. Suppositorium

| Composition: | /NVa/$^2$ cyclosporin | 1.500 kg |
| --- | --- | --- |
| | Arlasolve DMI | 1.500 kg |
| | Montanide 103 | 1.000 kg |
| | Axol L61 | 1.500 kg |
| | Gilugel CAO | 0.500 kg |
| | Witepsol H5 | up to 9.000 litres |

Method of preparation:

Axol L61 is mixed with Witepsol H5 at 55° C. and Gilugel CAO is disperged into the homogenous mixture. A solution of /NVa/$^2$ cyclosporin in Arlasolve DMI and Montanide 103 are added and the solution is stirred until cooling down to ambient temperature. The preparation is filled on a suitable device into gelatine suppositories of the following sizes:

No. 75 (=675 mg/NVa/$^2$ cyclosporin)

No. 15 (=150 mg/NVa/$^2$ cyclosporin)

No. 5 (=50 mg/NVa/$^2$ cyclosporin)

4. Cream

| Composition: | cyclosporin | 2.000 g |
| --- | --- | --- |
| | 1,3-dimethyl-2-imidazolidinon | 10.000 g |
| | Axol C62 | 40.000 g |
| | Gilugel ALM | 20.000 g |
| | Water | up to 100.000 g |

Method of preparation:

Axol C62 is heated to 65° C. and mixed with Gilugel ALM. The mixture is added to a solution of cyclosporin in 1,3-dimethyl-2-imidazolidinone and stirred in a turbo-homogenizer. Water heated to 70° C. is added at the same time. After the prescribed volume is reached the mixture is stirred by a frame stirrer until cooling down to ambient temperature. The mixture is then filled into containers with mechanical dosage aplicator SP30.

5. Oral concentrate

| Composition: | cyclosporin | 10.000 kg |
| --- | --- | --- |
| | ethanol | 8.000 kg |
| | Montanide 103 | 15.000 kg |
| | Gilugel MIG | 15.000 kg |
| | Miglyol 812 | up to 100.000 litres |

Method of preparation:

Cyclosporin is dissolved in ethanol and mixed with Montanide 103. Miglyol 812 is mixed with Gilugel MIG. The cyclosporin solution is added to oil fraction and the mixture is homogenized. The preparation (100 mg/ml) is applied diluted by water or a suitable drink.

6. Oral concentrate

| Composition: | cyclosporin | 10.000 kg |
| --- | --- | --- |
| | Arlasolve DMI | 15.000 kg |
| | Montanide 103 | 20.000 kg |
| | Axol C62 | 10.000 kg |
| | Gilugel MIG | 10.000 kg |
| | Miglyol 812 | up to 100.000 litres |

Method of preparation:

Axol C62 is heated to 65° C. and mixed with Miglyol 812. To the homogenous mixture is added the solution of cyclosporin in Arlasolve DMI and Montanide 103, than is stirred until cooling down to ambient temperature. In the mixture is disperged Gilugel MIG by colloid mill. The preparation is filled to gelatine capsules or in the suitable containers.

INDUSTRIAL APPLICABILITY

The invention is usable in pharmaceutical industry in manufacturing of immunosuppressive preparations and treating of autoimmune diseases.

We claim:

1. Pharmaceutical preparations with N-methylated cyclic undecapeptides characterized by the following composition: 0.1 to 20 weight parts of compounds /A/ from a group of cyclosporines, 0.3 to 60 weight parts of emulsifiers /B/ containing anhydromannitol oleylether and/or lactoglycerides and/or citroglyceride, 0.1 to 10 weight parts of emulsion stabilizer /C/ having aluminum-magnesium hydroxystearate of empirical formula $Al_5Mg_{10}(OH)_{31} \cdot (C_{17}H_{35}COO)_4$ in a form of lipogel, and 0.2 to 40 weight parts of solvent /D/ containing 1,4:3,6-dianhydro-2,5-di-O-methyl -D-glucitole and/or 1,3,-dimethyl-2-imidazolidinone, wherein the ratio A:B equals 1:0.5 to 1:30.

2. Pharmaceutical preparations according to claim 1, characterized by the presence of physiologically acceptable carrier based on synthetic or plant oil with interfacial tension in the range 10 mN.m$^{-1}$–25 mN.m$^{-1}$.

3. Pharmaceutical preparations according to claim 1, characterized by the fact that the compounds from the group of cyclosporins are either cyclosporin or /NVa/$^2$ cyclosporin.

4. Pharmaceutical preparations according to claim 1, characterized by the fact that the lactoglyceride or citroglyceride contain at least 90% of compound of the general formula:

where at least one of $R_1$, $R_2$, and $R_3$ substituents represents a lactic acid or citric acid moiety, one represents a fatty acid moiety, $C_{14}$ to $C_{18}$ and the remainder is selected from the group consisting of lactic acid moiety, citric acid moiety, fatty acid moiety $C_{14}$ to $C_{18}$ and hydrogen.

5. Pharmaceutical composition according to claim 1, wherein the preparation is for internal use.

6. Pharmaceutical composition according to claim 1, wherein the preparation is for internal use.

* * * * *

UNITED STATES PATENT AND TRADEMARK OFFICE
CERTIFICATE OF CORRECTION

PATENT NO. : 5,670,478
DATED : September 23, 1997
INVENTOR(S) : Stuchlik, et al.

It is certified that error appears in the above-indentified patent and that said Letters Patent is hereby corrected as shown below:

In claim 5, column 12, lines 8-9, please delete [Pharmaceutical composition according to claim 1, wherein the preparation is for internal use] and substitute --Medical preparations according to claim 1 for external application, characterized by content of 1,3-dimethyl-2-imidazolidinone used as a solvent--.

Signed and Sealed this

Eleventh Day of August 1998

Attest:

BRUCE LEHMAN

*Attesting Officer*  *Commissioner of Patents and Trademarks*